United States Patent [19]

Bendiner

[11] Patent Number: 5,840,249
[45] Date of Patent: Nov. 24, 1998

[54] PRESERVATIVE FOR ORGANIC MATERIALS

[76] Inventor: Bernard Bendiner, 326 Woodsedge, Suite B, Michigan City, Ind. 46360

[21] Appl. No.: 807,426

[22] Filed: Feb. 28, 1997

[51] Int. Cl.⁶ .............................. A61K 7/00; D21C 5/02; D21C 9/00; B01J 19/00
[52] U.S. Cl. ........................... 422/28; 424/401; 424/405; 162/5; 162/9; 422/40
[58] Field of Search .............................. 162/5, 9; 422/28, 422/40; 106/15.05; 424/405, 401

[56] References Cited

U.S. PATENT DOCUMENTS

| | | |
|---|---|---|
| 2,703,754 | 3/1955 | Myers . |
| 3,248,277 | 4/1966 | Gartner . |
| 3,808,089 | 4/1974 | Von Koeppen . |
| 3,822,178 | 7/1974 | Von Koeppen et al. . |
| 4,202,878 | 5/1980 | Ritze . |
| 4,570,573 | 2/1986 | Lohman . |
| 4,654,207 | 3/1987 | Preston . |
| 5,412,090 | 5/1995 | Bendiner ................................... 536/56 |

FOREIGN PATENT DOCUMENTS

| | | |
|---|---|---|
| 131681 | 5/1946 | Australia . |
| 940250 | 10/1963 | United Kingdom . |

*Primary Examiner*—Thurman K. Page
*Assistant Examiner*—S. Howard
*Attorney, Agent, or Firm*—Brinks, Hofer, Gilson & Lione

[57] ABSTRACT

A method for improving products such as toothpaste, shampoo, soap, detergent and lotions or creams and such improved products. The products are improved by adding a hydrous cellulose pulp that has an unlimited shelf life to the product. The hydrous cellulose pulp is resistant to decomposition and can be produced either by recycling waxed paper or through a process that begins with virgin vegetable constituents and wax. During the defibering process an emulsifier is added to the slurry and its temperature is elevated to 150°–190° Fahrenheit.

37 Claims, No Drawings

PRESERVATIVE FOR ORGANIC MATERIALS

BACKGROUND OF THE INVENTION

This invention relates to a non-toxic preservative and a process for forming the non-toxic preservative. The non-toxic preservative can be added to the slurry during the paper pulping process or sprayed on the wet lap pulp in paper making process employing wet lap pulp. The preservative of this invention can also be applied to chip piles and to newly cut lumber. Another use for the preservative of this invention is to apply it to trees and bushes. Still another use is to use it in water based products such as paints and varnishes.

In the paper making industry huge wood chip piles are produced for future use in the paper making process. The wood chip piles are often stored for long periods and deterioration. Sugar present in the wood fiber is attacked by bacteria which lowers the pH, when the pH is low the wood becomes vulnerable to attack by fungi. There is great amounts of heat produced in this process and chip piles have been known to ignite as a result. In the usual paper making process biocides are added to the slurry in the pulper. The biocides slow the deteration of the hydrous cellulose pulp material but does not stop it. In some paper making process the slurry is poured from the pulper and spread into sheets. Wet lap pulp is the term used to identify these sheets of hydrous cellulose pulp material as it emerges from a paper making pulper during the paper making process. Wet lap pulp has a very short shelf life and thus its usefulness in the non paper industry is limited. The biocides that are added to the slurry in the pulper or sprayed on the wet lap pulp are poisonous and thus the hydrous cellulose pulp material can not be used in many consumer products especially products for human consumption. Not only are the biocides not effective they are poisonous and thus present a hazard.

Most paper is made from plant fiber, most often wood, in a process that separates the cellulose from the other plant fiber material. Cellulose, the major constituent of plant fibers, is a carbohydrate. Carbohydrates are convertible into glucose by hydrolysis, a chemical process of decomposition. Under appropriate conditions the bacteria present in the paper making process contributes to and hastens decomposition. As a result, when cellulose pulp material is maintained in a hydrous state it has a very short shelf life.

In the paper making process, water is driven from the cellulose pulp and the remaining fiber is dried in a continuous operation. After the water has been removed, decomposition of the cellulose pulp ceases. However, if the process is suspended with the cellulose pulp in the hydrous state, for example over 90% water, the pulp has a very short shelf life. This short shelf life has been a major obstacle to the development of non-paper industry uses for hydrous cellulose pulp. Generally speaking, hydrous cellulose pulp is vulnerable to decomposition regardless of whether the pulp is derived from virgin vegetable constituents or from paper in a recycling operation.

Toxic biocides can be added to the process during the pulping stage which will inhibit decomposition but not stop it. The introduction of toxic biocides necessitates the addition of safety measures to protect the workers involved in the paper making process and also leaves a toxic residue in the wet lap pulp that may renders it unacceptable for use in consumer products especially consumer products that are consumed.

Furthermore, it is dangerous to spray toxic biocides on wet lap pulp after it has emerged from the pulper because the sprayed toxic biocides escape into and pollute the atmosphere thus creating a hazardous condition. Thus, the toxic biocides must be introduced into the paper making process during the pulping stage rather than being sprayed on the wet lap pulp after it has emerged from the pulping stage. As a result after a batch of wet lap pulp is produced that includes toxic biocides the pulping system must be cleaned to eliminate all biocides residues before a batch of wet lap pulp can be produced that is completely free of toxic biocides.

Corn starch is a very useful product when added to water for applying to the skin. However it must be uses very soon after it is mixed with water or it deteriorates. This short useful life is a serious drawback to the use of corn starch.

Waxed paper is customarily manufacture by forming the paper sheet first then treating the sheet with an application of wax coating, either in dry or liquid form. For example, molten paraffin wax is easily applied by continuously passing a paper sheet through a molten bath of wax, removing the excess and then chilling. Such waxed papers have excellent resistance to water vapor, are free from odor, taste and toxicity and are low in cost.

At one time waste waxed paper presented problems in the paper recycling industry. When waste wax paper was recycled waxy spots would appear on the resulting recycled paper and a wax coating would collect on the equipment thus fouling the recycling process. Consequently, the resulting recycled paper was considered inferior and it was often necessary to stop the process so that the equipment could be adequately cleaned.

The problem, with recycling waste waxed paper, was solved however by adding a water dispersible non-ionic emulsifiers to the pulper during the repulping phase of the recycling process. The mixture containing the emulsifier is mechanically agitated at a temperature sufficiently high to melt the wax, for example from approximately 150° to 190° Fahrenheit. This process produced an emulsified wax-fiber slurry having a solids consistency of from approximately 4% to 6% by weight. The hydrous cellulose pulp produced in this process for recycling waste waxed paper has the property of an unlimited shelf life. U.S. Pat. Nos. 3,808,089 and 3,822,178, the disclosures of which are incorporated herein by reference, fully discloses the above described process.

Various non-paper industry uses have been discovered for this hydrous cellulose pulp having an unlimited shelf life. For example, as a dispersed ingredient in toothpaste, shampoo, soap, detergent, lotions and cream products. Other non-paper industry uses that were discovered for this product were its use as artificial snow and mulch. The discovery of these non-paper industry uses of hydrous cellulose pulp having an unlimited shelf life is the subject matters of U.S. Pat. No. 5,412,090 that issued on May 2, 1995. U.S. Pat. No. 5,412,090 is hereby incorporated by reference as a part of this application. The hydrous cellulose pulp having an unlimited shelf life produced in accordance with the disclosure of U.S. Pat. No. 5,412,090 has a fiber content of about 4–6% by weight. Although this fiber content function, for example when included in shampoo as a scrubbing agent, traces of the fiber that are large enough to be visible -to the consumer is left on the hair. This residue, although harmless, is unacceptable to some consumers. For the above reasons there is a need for a hydrous cellulose material that has an unlimited shelf life, that does not leave a visible residue of pulp that could render the product in which it is contained unacceptable as a consumer product and is non toxic. It was found that if the hydrous cellulose pulp formed in accordance with U.S. Pat. No. 5,412,090 is filtered, for example with a 2 micrometer filter the non-toxic filtrate contains about 0.67% hydrous cellulose pulp, in the form of minute wax coated fiber filaments and the filtrate is completely free of microorganisms. This non-toxic filtrate has been found to be an excellent water base for consumer products. This non toxic filtrate is the subject matter of co-pending application Ser. No. 08/808,212, filed on the same day as this application. The subject matter of this co-pending application Ser. No. 08/808,212 is hereby included by reference as a part of this application.

A food grade preservative commonly identified as potassium sorbate and technically identified as 2,4 Hexadienoic Acid is used for example as a preservative for food products such as pickles. Potassium sorbate is in the form of a dry powder and can be placed in solution with a water base ingredient.

There is a need for a non toxic product and method for preventing wet lap pulp from degrading and thus prolonging its shelf life.

Furthermore, there is a need for a non toxic preservative that can be sprayed on wet lap pulp that will prevent it from degrading and not contaminate the atmosphere or the wet lap pulp for use in consumer products.

A need has also become apparent for a preservative made from natural products that will stop the decomposition of carbohydrates in wet lap pulp to thereby extend its shelf life.

SUMMARY OF THE INVENTION

It is an object of this invention to utilize hydrous cellulose pulp having an unlimited shelf life in a process that will produce a natural ingredient preservative that is non toxic that can be added to the slurry in the pulper or sprayed on wet lap pulp to extend its shelf life and enable it to be used in consumer products.

It is another object of this invention to utilize the filtrate of hydrous cellulose pulp having an unlimited shelf life as the water base to which potassium sorbate is added to provide a preservative that can be added to the slurry in the pulper or sprayed on wet lap pulp as a replacement for the poisonous biocides.

It is a further object of this invention to provide a non-toxic preservative that can be sprayed on wet lap pulp that will extend the shelf life of the wet lap pulp sufficient to allow it to be utilized for non-paper industry processes and products.

This invention consists of a process for producing a non toxic preservative that can be sprayed on wet lap pulp that will extend the shelf life of the wet lap pulp.

This invention consists of applying the preservative of this invention to the slurry in the pulper in place of the biocides.

This invention consists of applying the preservative of this invention to chip piles and to new lumber.

This invention consists of applying the preservative of this invention to leaves and bushes to prevent mold and deterioration of the plant.

This invention consists of utilizing the preservative of this invention as the base in water base products such as paints and varnishes.

This invention further consist of a process in which the filtrate of hydrous cellulose pulp that has an unlimited shelf life is used as the water base for a liquid preservative that includes potassium sorbate.

This invention further consist of the mixture of the preservative of this invention with corn starch to extend the useful life of corn starch in liquid form.

This invention also includes a process for producing hydrous cellulose pulp in a process including wax paper and an emulsifier along with heat sufficient to melt the wax to thus provide a micro-molecular film on the fiber, filtering the resulting hydrous cellulose pulp and combining the filtrate with potassium sorbate to produce a non-toxic liquid preservative that can be sprayed on wet lap pulp and extend its shelf life.

It is a objective of this invention to produce a non toxic preservative through a process that includes the steps of repulping waxed paper in a process requiring an emulsifier and heat sufficient to melt the wax to thus provide a micro-molecular film on the fiber resulting from the repulping process, filter out the larger fiber strands, blend the filtrate such that the minute film coated particles become dispersed in the liquid and then combining the filtrate with a food quality preservative which results in a liquid preservative that can be sprayed on wet lap pulp which can then be used in processes for producing non toxic consumer products.

DETAILED DESCRIPTION OF THE PREFERRED EMBODIMENT

During the emulsification phase, of the wax paper recycling process used in practicing this invention, substantial quantities of wax are present from the waste waxed paper. However, this wax does not contaminate or coat the equipment even when slurries containing the emulsified product are cooled. When making waxed paper, very little wax penetrates below the surface of the un-waxed sheet of paper. However, during the emulsification phase of recycling, the paper is broken down into minute fiber filaments having irregularly shaped surfaces. Each of these minute filaments has a substantial surface area. Literally millions of fiber filaments are released from a relatively small piece of wax paper. Consequently, a piece of waxed paper having a waxed surface of 100 square inches, for example, releases fiber filaments into the emulsified slurry that have a surface area that may be as much as 1,000,000 times the original 100 square inches, or 10,000,000 square inches. The wax from the surface of the waxed paper, is melted during the emulsification phase and forms a very thin micro-molecular film on the fiber filaments. In addition to the minute fiber filaments there are numerous microorganisms from the water and other ingredients of the recycling process. The microorganisms would in the usual paper making process cause decommission of the process ingredients. However, in the process of this invention these microorganisms becomes coated with a very thin layer of wax which prevents them from causing decommission of other ingredients found in the process. This hydrous cellular pulp is 95% water, 4.67% fiber and 0.32% wax. The hydrous cellular pulp is then filtered through a 2 micrometer (0.000002 meters) filter and the resulting filtrate is then used as the water base in products such as toothpaste, shampoo, soap, detergent, lotions and cream products.

This filtrate is also used as an ingredient of a liquid preservative of this invention. The liquid preservative of this invention can be sprayed on sheets of newly produced wet lap pulp after it has been spread into sheets and or baled. This filtrate is 99% water, 0.68 fiber and 0.32% wax.

The filtrate is free of microorganisms such as bacteria and fungi, possesses an unlimited shelf life, and may be produced either by recycling waste waxed paper, new waxed paper or by processing virgin vegetable constituents in the presence of wax during the emulsification phase of the defibering process.

A protective barrier is also believed to form around the molecular structure of the water. The filtrate, which is 99% water, and contains minute portions of fiber coated with a thin micro-molecular layer of wax derived from this process is non toxic and has an unlimited shelf life and thus can be utilized as the water base for products and provide the product with an unlimited shelf life.

In accordance with this invention, an example of the starting waxed paper that can be used is the type used in bakeries and deli-contestants to wrap food products. Waxed paper of this type is coated with a food grade paraffin wax, designated as a dry wax. Waste waxed paper can be used in the preferred embodiment and is obtained directly from the paper producing facilities. For example, trimmings from a trimming machine or wax paper that did not meet required test standards may be used. Such waxed paper is free of printing and thus is clean. The waxed paper is added to a pulper. A pulper is basically a vat for receiving a material that can be agitated by mechanical means and includes means to control the temperature. The process of pulping is essentially one of separating cells from intercellular material. It should be understood that any equipment such as a conventional high speed pulper may be used. The temperature of the wax-containing fiber slurry is raised to a temperature above the melting point of the wax and beating is continued until the wax and fiber are released into the aqueous solution. The resulting water-fiber slurry can then be subjected to a washing process to remove any impurities. Newly manufactured wax paper does not need this washing process.

The process of the present invention encompasses the use of 100% waxed paper stock having a wax content of up to 30% by weight. However, non-waxed waste paper, in modest proportions can be used without affecting the outcome. Non waxed fiber products can be used as a starting product and a paraffin wax in the correct ratio to fiber added. The use of waxed paper as a starting point has the advantage that it contains the proper ratio of fiber to wax and it is available at economical rates.

A water soluble non-ionic emulsifier is added to the pulper during the pulping phase of the paper making or recycling process. The water soluble non-ionic emulsifier being from the group consisting of: polyethylene glycol ethers of hydrophobic alcohols; alkylphenoxy polyethoxyethanols; fatty acid amides and mixtures thereof. The water soluble non-ionic emulsifier must also meet specific emulsion stability standards. The preferred water soluble non-ionic emulsifiers include: ethoxylated aliphatic alcohols wherein the alcohol is a hydrophobic secondary alcohol having from 11 to 15 carbon atoms and wherein the average molar ratio of ethylene oxide to hydrophobic alcohol is in a range of 5:1 to 15:1; ethoxylated alkyl phenols in which the ratio of moles of ethylene oxide per mole or ethylene oxide per mole of alkyl phenol is in the range of 7–8 inclusive; ethoxylated alkyl phenols in which the alkyl substituent is linear; and the fatty acid amide diethanol amine condensates derived from a member selected from the group consisting of myristic acid, lauric acid, palmitic acid, stearic acid and mixtures thereof.

After the process for producing the hydrous cellulose pulp has been completed, it is filtered through a very fine filter, for example a 2 micrometer (0.000002 meters) filter to remove the larger portions of hydrous cellulose pulp, leaving a filtrate that is free of microorganism and includes only minute fiber portions that are coated with a very thin layer of wax. Although a 2 micrometer filter is used in the preferred embodiment it should be understood that a very fine filter is required but it need not be precisely 2 micrometers. The filtrate has a very low viscosity and can be readily sprayed through conventional nozzles.

Potassium sorbate, in powder form, is then mixed with the filtrate, at a ratio in the range of 0.1%–5% by weight, and citric acid is added until the pH is 6.5 or below. The term pH indicates the hydrogen ion concentration of a solution, which is a measure of the solution's acidity. The pH of pure water is 7.0. If acid is added to pure water, an excess of H3O+ ions is formed and the acid solution has a pH ranging from 6 for a weak acid to 1 for a strong acid. Inversely, a basic solution has a low concentration of $H_3O^+$ ions and an excess of OH− ions, and the pH ranges from 8 for a weak base to 14 for a strong base. Thus, the resulting preservative is a weak acid. The mixture is blended to suspend the potassium sorbate evenly throughout the filtrate.

The preservative is then sprayed on the layered or baled wet lap pulp. The wet lap pulp can then be stored and or shipped in, for example plastic bags, to processing facilities where it can undergo further processing. The wet lap pulp can be maintained in its moistened state and it will not decompose or decay. The preservative can be sprayed on the wet lap pulp and even though some preservative will escape into the atmosphere this does not pose a health hazard to the workers applying the spray or the area where the spraying is done.

Wax from the original waste waxed paper is present on minute portions of fiber that are dispersed in the preservative. The preservative coasts the fibers contained in the wet lap pulp and prevents the wet lap pulp from decaying. The food grade preservative Potassium sorbate functions as a non-toxic ingredient that is carried by the slightly acid water base that alone has an unlimited shelf life. This unique combination of ingredients results in a preservative that can be easily sprayed on an organic product that is to be stored or preserved for use in the non-paper industry. Although wax is present on the minute fibers filaments, in a very thin coating, this wax does not hinder the use of the wet lap pulp in any manner.

While the invention has heretofore been described in detail with particular reference to specific products, it is to be understood that variation, modifications and the use of equivalents can be effected without departing from the scope of this invention. It is, therefore, intended that such changes and modifications be covered by the following claims.

I claim:

1. A process for producing a preservative for applying to organic matter that will prevent the decomposition of the organic matter and enable it to be used for industrial purposes, comprising the steps of:

producing a decomposition resistant hydrous cellulose pulp, the individual fibers of which are coated with a thin wax film;

(a) filtering the decomposition resistant hydrous cellulose pulp through a very fine filter;

(b) adding potassium sorbate to the filtrate at a ratio of one part of filtrate to potassium sorbate that is in the range of 0.1% to 5% by weight;

(c) adding citric acid to the mixture in amounts to reduce the pH to 6.5 or lower.

2. The process as set forth in claim 1 wherein the organic matter being preserved is the slurry contained in the pulper during the paper making process.

3. The process as set forth in claim 1 wherein the organic matter being preserved is wet lap pulp.

4. The process as set forth in claim 1 wherein the organic matter being preserved is wood chip piles.

5. The process as set forth in claim 1 wherein the organic matter being preserved is cut lumber.

6. The process as set forth in claim 1 wherein the organic matter being preserved is corn starch.

7. The process as set forth in claim 1 wherein the organic matter being preserved is the leaves of living plants.

8. The process as set forth in claim 1 wherein the filter through which the decomposition resistant hydrous cellulose pulp passes has opening of about 2 micrometers.

9. The process as set forth in claim 2 wherein the filter through which the decomposition resistant hydrous cellulose pulp passes has opening of about 2 micrometers.

10. The process as set forth in claim 1 wherein in the process for producing the decomposition resistant hydrous cellulose pulp a water soluble non-ionic emulsifier that meets the following emulsion stability standards is used:

ethoxylated aliphatic alcohols wherein the alcohol is a hydrophobic secondary alcohol having from 11 to 15 carbon atoms and wherein the average molar ratio of ethylene oxide to hydrophobic alcohol is in a range of 5:1 to 15:1.

11. The process as set forth in claim 2 wherein in the process for producing the decomposition resistant hydrous cellulose pulp a water soluble non-ionic emulsifier that meets the following emulsion stability standards is used:

ethoxylated aliphatic alcohols wherein the alcohol is a hydrophobic secondary alcohol having from 11 to 15 carbon atoms and wherein the average molar ratio of ethylene oxide to hydrophobic alcohol is in a range of 5:1 to 15:1.

12. The process as set forth in claim 3 wherein in the process for producing the decomposition resistant hydrous cellulose pulp a water soluble non-ionic emulsifier that meets the following emulsion stability standards is used:

ethoxylated aliphatic alcohols wherein the alcohol is a hydrophobic secondary alcohol having from 11 to 15 carbon atoms and wherein the average molar ratio of ethylene oxide to hydrophobic alcohol is in a range of 5:1 to 15:1.

13. The process as set forth in claim 4 wherein in the process for producing the decomposition resistant hydrous cellulose pulp a water soluble non-ionic emulsifier that meets the following emulsion stability standards is used:

ethoxylated aliphatic alcohols wherein the alcohol is a hydrophobic secondary alcohol having from 11 to 15 carbon atoms and wherein the average molar ratio of ethylene oxide to hydrophobic alcohol is in a range of 5:1 to 15:1.

14. The process as set forth in claim 1 wherein in the process for producing the decomposition resistant hydrous cellulose pulp a water soluble non-ionic emulsifier that meets the following emulsion stability standards is used:

ethoxylated alkyl phenols in which the ratio of moles of ethylene oxide per mole or ethylene oxide per mole of alkyl phenol is in the range of 7–8 inclusive.

15. The process as set forth in claim 2 wherein in the process for producing the decomposition resistant hydrous cellulose pulp a water soluble non-ionic emulsifier that meets the following emulsion stability standards is used:

ethoxylated alkyl phenols in which the ratio of moles of ethylene oxide per mole or ethylene oxide per mole of alkyl phenol is in the range of 7–8 inclusive.

16. The process as set forth in claim 3 wherein in the process for producing the decomposition resistant hydrous cellulose pulp a water soluble non-ionic emulsifier that meets the following emulsion stability standards is used:

ethoxylated alkyl phenols in which the ratio of moles of ethylene oxide per mole or ethylene oxide per mole of alkyl phenol is in the range of 7–8 inclusive.

17. The process as set forth in claim 4 wherein in the process for producing the decomposition resistant hydrous cellulose pulp a water soluble non-ionic emulsifier that meets the following emulsion stability standards is used:

ethoxylated alkyl phenols in which the ratio of moles of ethylene oxide per mole or ethylene oxide per mole of alkyl phenol is in the range of 7–8 inclusive.

18. The process as set forth in claim 1 wherein in the process for producing the decomposition resistant hydrous cellulose pulp a water soluble non-ionic emulsifier that meets the following emulsion stability standards is used:

ethoxylated alkyl phenols in which the alkyl substituent is linear and the fatty acid amide diethanol amine condensates derived from a member selected from the group consisting of myristic acid, lauric acid, palmitic acid, stearic acid and mixtures thereof.

19. The process as set forth in claim 2 wherein in the process for producing the decomposition resistant hydrous cellulose pulp a water soluble non-ionic emulsifier that meets the following emulsion stability standards is used:

ethoxylated alkyl phenols in which the alkyl substituent is linear and the fatty acid amide diethanol amine condensates derived from a member selected from the group consisting of myristic acid, lauric acid, palmitic acid, stearic acid and mixtures thereof.

20. The process as set forth in claim 3 wherein in the process for producing the decomposition resistant hydrous cellulose pulp a water soluble non-ionic emulsifier that meets the following emulsion stability standards is used:

ethoxylated alkyl phenols in which the alkyl substituent is linear and the fatty acid amide diethanol amine condensates derived from a member selected from the group consisting of myristic acid, lauric acid, palmitic acid, stearic acid and mixtures thereof.

21. The process as set forth in claim 4 wherein in the process for producing the decomposition resistant hydrous cellulose pulp a water soluble non-ionic emulsifier that meets the following emulsion stability standards is used:

ethoxylated alkyl phenols in which the alkyl substituent is linear and the fatty acid amide diethanol amine condensates derived from a member selected from the group consisting of myristic acid, lauric acid, palmitic acid, stearic acid and mixtures thereof.

22. A preservative for organic matter comprising: a filtrate of a decomposition resistant hydrous cellulose pulp material;

potassium sorbate, in the range of 0.1%–5% by weight of the filtrate; and citric acid sufficient to lower the pH to 6.5 or lower.

23. The preservative as set forth in claim 22 wherein in the organic matter being preserved is wet lap pulp.

24. The preservative as set forth in claim 22 wherein the filter through which the decomposition resistant hydrous cellulose pulp passes has opening of about 2 micrometers.

25. The preservative as set forth in claim 23 wherein the filter through which the decomposition resistant hydrous cellulose pulp passes has opening of about 2 micrometers.

26. The preservative as set forth in claim 22 wherein in the process for producing the decomposition resistant hydrous cellulose pulp a water soluble non-ionic emulsifier that meets the following emulsion stability standards is used:

ethoxylated aliphatic alcohols wherein the alcohol is a hydrophobic secondary alcohol having from 11 to 15 carbon atoms and wherein the average molar ratio of ethylene oxide to hydrophobic alcohol is in a range of 5:1 to 15:1.

27. The preservative as set forth in claim 23 wherein in the process for producing the decomposition resistant hydrous cellulose pulp a water soluble non-ionic emulsifier that meets the following emulsion stability standards is used:

ethoxylated aliphatic alcohols wherein the alcohol is a hydrophobic secondary alcohol having from 11 to 15 carbon atoms and wherein the average molar ratio of ethylene oxide to hydrophobic alcohol is in a range of 5:1 to 15:1.

28. The preservative as set forth in claim 24 wherein in the process for producing the decomposition resistant hydrous cellulose pulp a water soluble non-ionic emulsifier that meets the following emulsion stability standards is used:

ethoxylated aliphatic alcohols wherein the alcohol is a hydrophobic secondary alcohol having from 11 to 15 carbon atoms and wherein the average molar ratio of ethylene oxide to hydrophobic alcohol is in a range of 5:1 to 15:1.

29. The preservative as set forth in claim 25 wherein in the process for producing the decomposition resistant hydrous cellulose pulp a water soluble non-ionic emulsifier that meets the following emulsion stability standards is used:

ethoxylated aliphatic alcohols wherein the alcohol is a hydrophobic secondary alcohol having from 11 to 15 carbon atoms and wherein the average molar ratio of ethylene oxide to hydrophobic alcohol is in a range of 5:1 to 15:1.

30. The preservative as set forth in claim 22 wherein in the process for producing the decomposition resistant hydrous cellulose pulp a water soluble non-ionic emulsifier that meets the following emulsion stability standards is used:

ethoxylated alkyl phenols in which the ratio of moles of ethylene oxide per mole or ethylene oxide per mole of alkyl phenol is in the range of 7–8 inclusive.

31. The preservative as set forth in claim 23 wherein in the process for producing the decomposition resistant hydrous cellulose pulp a water soluble non-ionic emulsifier that meets the following emulsion stability standards is used:

ethoxylated alkyl phenols in which the ratio of moles of ethylene oxide per mole or ethylene oxide per mole of alkyl phenol is in the range of 7–8 inclusive.

32. The preservative as set forth in claim 24 wherein in the process for producing the decomposition resistant hydrous cellulose pulp a water soluble non-ionic emulsifier that meets the following emulsion stability standards is used:

ethoxylated alkyl phenols in which the ratio of moles of ethylene oxide per mole or ethylene oxide per mole of alkyl phenol is in the range of 7–8 inclusive.

33. The preservative as set forth in claim 25 wherein in the process for producing the decomposition resistant hydrous cellulose pulp a water soluble non-ionic emulsifier that meets the following emulsion stability standards is used:

ethoxylated alkyl phenols in which the ratio of moles of ethylene oxide per mole or ethylene oxide per mole of alkyl phenol is in the range of 7–8 inclusive.

34. The preservative as set forth in claim 22 wherein in the process for producing the decomposition resistant hydrous cellulose pulp a water soluble non-ionic emulsifier that meets the following emulsion stability standards is used:

ethoxylated alkyl phenols in which the alkyl substituent is linear and the fatty acid amide diethanol amine condensates derived from a member selected from the group consisting of myristic acid, lauric acid, palmitic acid, stearic acid and mixtures thereof.

35. The preservative as set forth in claim 23 wherein in the process for producing the decomposition resistant hydrous cellulose pulp a water soluble non-ionic emulsifier that meets the following emulsion stability standards is used:

ethoxylated alkyl phenols in which the alkyl substituent is linear and the fatty acid amide diethanol amine condensates derived from a member selected from the group consisting of myristic acid, lauric acid, palmitic acid, stearic acid and mixtures thereof.

36. The preservative as set forth in claim 24 wherein in the process for producing the decomposition resistant hydrous cellulose pulp a water soluble non-ionic emulsifier that meets the following emulsion stability standards is used:

ethoxylated alkyl phenols in which the alkyl substituent is linear and the fatty acid amide diethanol amine condensates derived from a member selected from the group consisting of myristic acid, lauric acid, palmitic acid, stearic acid and mixtures thereof.

37. The preservative as set forth in claim 31 wherein in the process for producing the decomposition resistant hydrous cellulose pulp a water soluble non-ionic emulsifier that meets the following emulsion stability standards is used:

ethoxylated alkyl phenols in which the alkyl substituent is linear and the fatty acid amide diethanol amine condensates derived from a member selected from the group consisting of myristic acid, lauric acid, palmitic acid, stearic acid and mixtures thereof.

* * * * *